United States Patent [19]

Hargest, III et al.

[11] 4,298,001
[45] Nov. 3, 1981

[54] FLUID FLOW CONNECTOR UNIT AND METHOD

[76] Inventors: Thomas S. Hargest, III, 1078 Winslow Dr., Charleston, S.C. 29412; William C. Ryan, Jr., 1583 Sanford Rd., Charleston, S.C. 29407

[21] Appl. No.: 176,287

[22] Filed: Aug. 8, 1980

[51] Int. Cl.³ .............................................. A61M 3/00
[52] U.S. Cl. ................................. 128/247; 128/214 R
[58] Field of Search ................... 128/247, 214 R, 213; 220/352, 356

[56] References Cited

U.S. PATENT DOCUMENTS

| 3,394,954 | 7/1968 | Sarns | 128/247 X |
| 3,731,684 | 5/1973 | Spiegel | 128/247 |
| 3,987,930 | 10/1976 | Fuson | 128/214 R X |
| 4,201,208 | 5/1980 | Cambio, Jr. | 128/247 |

Primary Examiner—John D. Yasko
Attorney, Agent, or Firm—Wellington M. Manning, Jr.; Luke J. Wilburn, Jr.

[57] ABSTRACT

A multiple access fluid connector unit having two connector elements adapted for connection to a source of fluid or a fluid administration device and sealed on an opposite end. A plurality of spacially separate access ports are provided along the length of the elements, in communication with a fluid manifold that extends along the element. An outer end of each port has a removable cover to maintain the port sterile prior to use. Ports on one element are associable with ports on the other element to provide fluid flow through the unit. After association of two ports, when desirable to disconnect, the associated ports are severed from the elements and the element is resealed adjacent the cut. Two further of the sterile ports can thereafter be uncovered and used to reinstitute fluid flow through the unit.

12 Claims, 4 Drawing Figures 4,298,001

FLUID FLOW CONNECTOR UNIT AND METHOD

BACKGROUND OF THE INVENTION

Oftentimes in the medical treatment of patients, it becomes necessary to intravenously or otherwise infuse a fluid into the body of the patient over a protracted period of time. Normally under such circumstances, a tube or catheter is secured within the particular body portion of the patient and the desired fluid is then arranged to flow through the catheter or tube via an intermediate connector unit, such that the catheter or tube can remain in place during periods of disconnection. Additional fluid supply or different fluid supply can thereafter be operatively connected thereto as desired. Obviously in those situations where it becomes necessary to disconnect the fluid supply or reinstitute fluid flow through the tube or catheter, care must be taken to avoid contamination of the patient. It is thus necessary to maintain sterile conditions, such that, bacteria are not introduced into the patient's body that could lead to infection. While obviously contamination could occur by removal of a sterile connector from its package, the present concern and context of sterility is that the unit not have been previously used unless it has been resterilized following such use.

Reconnection of a fluid supply to a tube, catheter or the like via a reuseable connector unit, is accomplished only after the connector is physically cleaned with special solutions such that any bacteria present are supposedly killed. In general, the physical cleaning operation is particularly tedious and time consuming without any guarantee that the connector is in fact sterile after cleaning. Should the connector not be sterile after cleaning, during reuse of same, the patient could become infected. In fact, in certain instances the connector unit is manipulated by patients or others in home bound situations. Resterilization of the connector units is distasteful to these persons to the point that without proper supervision, there is a tendency to cut corners, usually resulting in some degree of patient infection.

In order to reduce the problems incident to resterilization of reuseable connectors, the medical industry has generally moved from the reuseable connector to disposable, presterilized connectors which have gained considerable acceptance. When, however, repeated interruption of the fluid connection is necessary, such as with peritoneal dialysis, the act of inserting the presterilized, disposable connector can generate the same general problems as resterilization of a previously used component, in that the disposable unit could be reused, or attempts made to resterilize same for further use.

Clearly with any type of connector there must be replacement at some interval and at such times, sterile procedures should always be utilized. For example, in a situation where a patient must connect daily, such as a patient requiring peritoneal dialysis, utilizing state of art connectors, the patient undergoes 14 exposures per week, one per connection and one per disconnection where a non-sterile connector could be inadvertently or otherwise reused.

The present device, while not alleviating totally the need for sterile procedure clearly can be utilized to reduce same to a minimal amount. For example, utilizing a device according to teachings of the present inventon, the patient requiring peritoneal dialysis could be exposed to only two situations per week where conventional sterile procedures must be utilized, one when the old unit is disconnected and the other when a new multiple sterile connector unit is connected thereto. Such would affect a reduction of potential for infection from 14 instances to 2 instances, or approximately an 85% reduction in potential bacterial infection due to non-sterile connector conditions. Similar situations exist for chemotherapy, hyperalimentation, and other similar procedures.

In essence therefore, the present invention eliminates the problem of resterilization, and, in essence, provides a series of disposable, presterilized, interrelated connectors which are constantly ready for use. The subject matter of the present invention is neither taught nor suggested by any known prior art.

SUMMARY OF THE INVENTION

It is an object of the present invention to provide a presterilized medical connector unit that may be utilized between a source of fluid and a means for introducing fluid into the body of a patient.

Another object of the present invention is to provide an improved disposable medical fluid connector device.

Still further another object of the present invention is to provide an improved medical fluid transporting unit that has a plurality of connector ports thereon, each of which is presterilized and awaits operative association with a further connector port to permit disconnection and reconnection of the connector device under sterile conditions without a possibility of reuse of a connector port.

Yet another object of the present invention is to provide an improved medical fluid connector device which is incrementally disposable.

Generally speaking, the apparatus of the present invention relates to a multiple access sterile connector unit comprising a pair of connector elements, each element having a fluid manifold extending along the length of same, one end of said element being sealed and an opposite end of said element being operatively associable with one of a source of fluid and fluid applicator means, each of said connector elements further having a plurality of spacially separate access stations therealong and extending generally outwardly therefrom, said access stations defining a fluid passageway therethrough in communicaton with said fluid manifold and each access station having removable cover means received at an outer free end of same in association therewith to maintain said outer free end of said station sterile while said cover means is initialy received thereat, said access stations being adapted for single use operable association with an access station on the other of said connector elements to establish fluid flow through said unit, each of said elements further being adapted for removal of associated access stations when desired and subsequent reassociation of other stations, whereby fluid flow to a patient may be disrupted and reinstituted through sterile conditions.

More specifically, the apparatus of the present invention relates to a pair of connector elements, preferably molded of a synthetic polymeric material, thermoplastic in nature, such that, a portion of same may be severed while thermally sealing a portion of the unit adjacent the point of severance. Spaced along the length of the unit which serves as a manifold, are a plurality of outwardly extending access ports or stations which have fluid passageways therethrough in communication with the common manifold and an outer free end of which is individually covered in a presterilized condition with a removable cover means. With a like number of access ports on each of two connector elements, once a first pair is connected to provide fluid flow through the entire unit, and it becomes desirable or necessary to break the connection, the central manifold of each element may be severed adjacent the particular associated access ports while being thermally sealed thereat. The used access ports are thus disassociated from the connector elements, and the next two end access stations may be operatively associated after the respective cover means have been removed to reinstitute fluid flow thrugh connection unit. In such fashion, it is clearly known that the new access ports have been previously contaminated during the period of disconnection except, of course, during the brief period after the cover means is removed and prior to association with another port, which exposure is of course minimal and not generally considered critical.

Since it is desirable to avoid as much as possible the possibility of bacterial contamination incident to disruption and reinstitution of fluid flow, in a preferred embodiment, the connector unit according to teachings of the present invention is designed to prohibit disconnection of the access ports followed by a reconnection of same to the same or a different port. In particular, the access ports may be adopted with any type of closure means, where once the operative association or connection is made, it becomes impractical, if not impossible, to disassociate the connected ports. Instead, the connected ports would be severed from the ends of the individual connector elements and discarded. Disposability is thus assured for the preferred connector unit of the present invention and thus precludes the incidence of possible contamination.

According to one embodiment of the present invention, the respective connector elements may be manufactured for a particular end use, having incorporated therein the number of access ports or stations that would normally be required during the course of a particular treatment being administered to a patient. As such, once initial connection is made, with one connector element being associated with a source of fluid and the other connector element being associated with a means for administering the fluid, thereafter, during disruption and reinstitution of fluid flow, truly non-sterile conditions are encountered only when, and for the very short period of time, the cover means are removed from respective access stations and the access stations are brought into operative association.

The method of the present invention for administering fluid to a patient generally comprises the steps of locating a fluid administration means to present fluid to a particular body portion; providing a source of fluid; providing a pair of presterilized, associable connector elements, and associating one of said elements with said fluid administration means and the other of said elements with said source of fluid, each of said elements having a central fluid manifold that is sealed at one end and in fluid communication with said respective administration means on said source of fluid at an opposite end, said manifold having a plurality of spacially separate access ports secured thereto and extending outwardly therefrom, each said access port being in fluid communication with said manifold and having a removable cover means at an outer free end of same, which cover means maintains said access ports sterile while in place; said access ports of one element being associable with the access ports on the other of said elements; removing the cover means from the access ports of each connector nearest the sealed end of same and bringing said two end access ports into fluid communicating association, whereby fluid communication is established between said fluid supply and said patient; at a desired time, interrupting fluid flow to the patient by severing the manifold on each element between the associated access ports and a further access port and sealing the manifold adjacent thereto, whereby the associated access ports are removed from the elements; and when reinstitution of fluid flow is desired, removing the cover means for an access port on each element and bringing said two access ports into fluid communication association, whereby fluid flow to the patient is reinstituted without the possibility of reuse of a contaminated connector.

The number of disruptions and reconnections depends upon the number of access ports on the elements. Also, preferably the end access ports are employed each time a connection is made.

DESCRIPTION OF THE PREFERRED EMBODIMENTS

Figure 1:
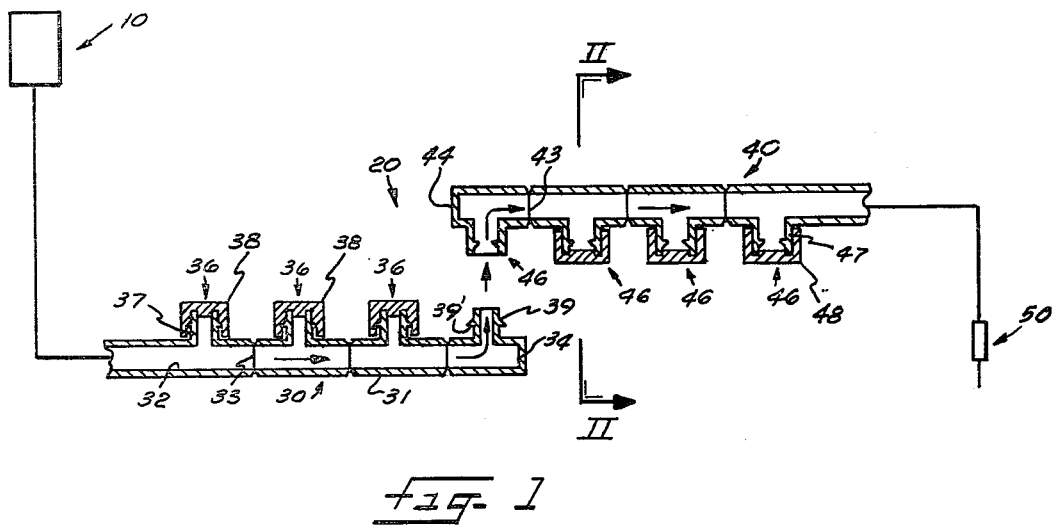
FIG. 1 of the drawings is a vertical cross-sectional view of the pair of connector elements that make up the connector unit according to teachings of the present invention, one of which is schematically shown associated with a source of fluid while the other of which is schematically shown associated with a fluid applicator means.
Figure 2:
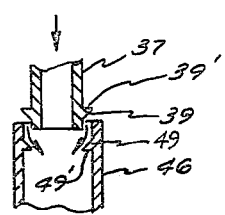
FIG. 2 is a partial vertical cross-sectional view of a portion of two access stations as illustrated in FIG. 1, to better demonstrate a preferred operative connection between same, such that, once connected, the disconnection of the access station is impractical.
Figure 3:
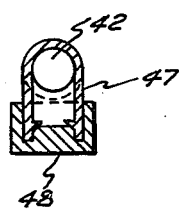
FIG. 3 is a vertical cross-sectional view of a portion of a connector element as illustrated in FIG. 1 taken along a line III—III.

Making reference to the Figures, preferred embodiments of the present invention will now be described in detail. In FIGS. 1 through 3, the connector unit of the present invention is illustrated in detail. Schematically speaking, FIG. 1 includes a source of fluids generally indicated as 10 having the connector unit of the present invention (shown disconnected) generally indicated as 20 located between the source of fluids 10 and a fluid administration means generally indicated as 50. Connector unit 20 includes a first connector element generally indicated as 30 and a second connector element generally indicated as 40. Applicator unit 30 includes an elongated body 31 that internally defines a fluid manifold 32 therealong. One end of body 31 (not shown) is open and is adapted for association with the source of fluid 10 while an opposite end of body 31 is sealed. Since the feature of the connector element for association with the source of fluids is conventional in the art, same has only been schematically illustrated. Located along the body 31 are a plurality of spacially separate access ports generally indicated as 36. Ports 36 are secured to body 31 and extend outwardly therefrom, preferably in a direction generally transverse to the direction of manifold 32, with side walls 37 of same defining a fluid passageway therethrough that communicates with manifold 32. When access ports 36 are not in use, a removable cover means 38 is received thereover, in such fashion to maintain the access ports 36 in a sterile condition for use at a later time. As illustrated in FIGS. 1 and 2, side wall 37 of access port 36 has an enlarged beveled surface 39 adjacent an outer free end of same which terminates at a shoulder 39', the purpose of which will be described hereinafter. As mentioned above, and illustrated in FIG. 1, the plurality of access ports 36 are spacially separate along body 31, and in a preferred embodiment, body 31 is provided with a thin wall section 33 located between each two access ports 36, such that, subsequent to use of a particular access port, appropriate means may be provided to thermally seal manifold 32 at the particular weakened wall section 33 and to sever body 31, removing the access port located outwardly therefrom.

A second connector element generally indicated as 40 is provided which likewise has a body 41 that internally defines common manifold 42 located along the length of same and having weakened wall sections 43 located between adjacent access ports generally indicated as 46. A forward free end of body 41 of element 40 is provided with a seal 44 while the opposite end is adapted for association with a fluid administration means generally indicated as 50 in a conventional fashion (not shown). Similarly to the connector element 30, the access ports 46 on connector element 40 are secured to body 41 and extend outwardly therefrom, preferably in a generally transverse direction. Walls 47 of ports 46 define a fluid passageway therethrough in communication with manifold 42 at one end and receive a cover means 48 at an outer free end before the port is used, such that the port is maintained in a sterile condition prior to use. To enable particular access ports 46 to be associated for a single use situation, with particular reference to FIGS. 2 and 4, the inner walls of ports 46 are provided with an inwardly protruding beveled section 49 which terminates at a shoulder 49'.

FIG. 2 particularly demonstrates one form of single use association between access ports 36 and 46. An access station 36 is being forced downwardly into a receiving access station 46. Complementary beveled surface 39 and 49, come into engagement, and as force is applied, due to resilience of the material from which the connector elements are produced, walls 37 and 47 respectively of ports 36 and 46 will be compressed and expanded, permitting surfaces 39 and 49 to pass each other. Thereafter walls 37 and 47 return to normal dimensions and shoulders 39' and 49' will abut to preclude dissassociation of the ports. Hence to disrupt fluid flow, it is necessary to sever the bodies 31 and 41 along respective thin wall sections 33 and 43 and reseal conduits 32 and 42. Associated ports 36 and 46 are thus removed from the connector unit whereby it is impossible for once associated ports to be reused after possible contamination. Thereafter, the cover elements 38 and 48 for the next adjacent ports 36, 46 respectively, may be removed and the exposed ports brought into association for further fluid flow in the manner shown in FIG. 2.

It should be understood, however, that any means may be utilized in conjunction with the particular access ports for operative connection of same in a fluid tight arrangement while precluding disassociation that would permit either or both of the access ports to be reused a second time when the sterility of same would be questionable. In fact independent means may be utilized to achieve the non-separable relationship, the ports could be thermally fused, or the like.

Figure 4:
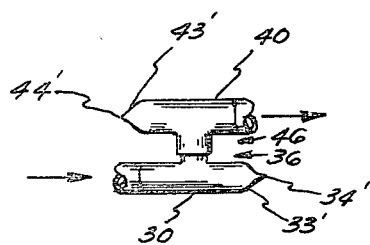
FIG. 4 is a side elevational view of a portion of two connector elements of the type illustrated in FIG. 1 shown connected after severance and sealing of a portion of the manifold.

According to teachings of the present invention therefore, making particular reference to FIG. 4, a portion of a connector unit is illustrated for which access ports have been removed and further access ports now in operative association. Assuming that the connector elements 30 and 40 of FIG. 1 had been brought together with the forwardmost access ports 36 and 46 in operative association, the fluid connection was disrupted as wall sections 33' and 43' and the then terminal ends 34' and 44' of the respective connectors sealed adjacent the cut. Previously associated access stations were thus removed from the unit, prohibiting their further use. After removing cover means 38 and 48 respectively from access ports 36 and 46 nearest newly sealed ends 34' and 44' of connectors 30 and 40, the mating access ports were brought together to association. At a time when it would become necessary to again disrupt fluid flow to the patient, a further severance and reseal would occur along the thin wall sections 33 and 43 to remove the connected ports as shown in FIG. 4 from the unit, and the reconnecting procedure would be repeated, if necessary.

In general use of the improved connected device according to the teachings of the present invention, where a repetitive disruption and reconnection of a fluid being infused into a patient is necessary, such as hyperalimentation, chemotherapy and peritoneal dialysis where the administrative unit 50 is a catheter, etc., that is secured within the stomach, etc., of a patient and extends outwardly therefrom, the source of fluid 10 and the catheter are respectively interconnected by association of connector units 30 and 40. Cover means 38 and 48 are removed from the forward or outermost access ports 36 and 46 and the two ports are brought into operative assocation such that, fluid flow is instituted between the source 10 and the administrative unit 50. Since as illustrated in FIG. 2, the access ports 36 and 46 are adapted, to preclude separation once the parts are brought into cooperative fluid flow association elements 30 and 40 must be severed and sealed about thin wall sections 33 and 43, if disruption of flow followed by reconnection is desired. Once the elements 30 and 40 are severed and resealed, the then forwardmost access ports, which would be the second access ports 36 and 46 counting in from the originally sealed ends of manifolds 32 and 42, would be uncovered and brought into association in locking fashion and whereby the fluid connection would be reinstituted. This procedure would be continued until such time as the procedure is no longer necessary or until such time as all of the access stations on the unit are utilized.

Any materials of construction may be utilized in manufacturing the apparatus of the present invention so long as the apparatus will function as intended. For example, the individual connector elements could be molded of synthetic polymeric materials that are thermoplastic in nature, and which is capable of being sterilized. Such is preferred to permit thermal resealing of the manifolds with severance of associated ports. Further, the entire unit would preferably be sterilized and packaged in such fashion that the sterile conditions are maintained until the unit is removed from the package.

Having described the present invention in detail, it is obvious that one skilled in the art will be able to make variations and modifications thereto without departing That which is claimed is:

1. A multiple access sterile connector unit comprising a pair of connector elements, each element having a body defining a fluid manifold extending along the length of same, one end of said element being sealed and an opposite end of said element being operably associable with one of a source of fluid and a fluid applicator means, each of said connector elements further having a plurality of spacially separate access ports located therealong and extending outwardly therefrom, said access ports defining a fluid passageway therethrough in communication with said fluid manifold, and each acess port having removable cover means at an outer free end of same in association therewith to maintain said outer free end of said port sterile while said cover means is initially received thereat, said access ports being adapted for operable association with an access port on the other of said connector elements to establish fluid flow through said unit, each of said elements further being adapted for removal of associated access ports when desired and subsequent reassociation of other ports, whereby fluid flow to a patient may be disrupted and reinstituted under sterile conditions.

2. A unit as described in claim 1 wherein at least said bodies of said connector elements are manufactured from a thermally sealable material, whereby associated access ports may be severed from said elements and said manifolds thermally sealed adjacent the point of severance.

3. A unit as described in claim 1 wherein said elements are molded of a thermoplastic thermally sealable material.

4. A unit as defined in claim 1 wherein said access parts are provided with means thereon to cooperate with means on an access port on said other of said elements to preclude separation after association of said ports.

5. A unit as defined in claim 4 wherein said means to preclude separation of said access ports include elements located thereon that interlock to permit association while resisting separation.

6. A unit as defined in claim 5 wherein one of said ports has a beveled protrusion around an end of same, terminating at a shoulder while the other of said ports has an inwardly protruding beveled surface terminating at a shoulder, said ports telescoping one within the other until said shoulders interlock.

7. A unit as defined in claim 1 wherein said cover means surrounds said outer free end of said access ports and extends at least partially along the length of same for a distance adequate to maintain said portion of said port to be associated with another port in a sterile condition until said cover means is removed.

8. A unit as defined in claim 2 wherein said bodies have thin walled sections therealong at points where same are to be severed and resealed.

9. An improved method of administering fluid to a patient over a protracted period of time where fluid connection is interrupted and reinstituted comprising the steps of:

(a) locating a fluid administration means to present fluid to a particular body portion;

(b) providing a source of fluid;

(c) providing a pair of presterilized, associable connector elements, and associating one of said elements with said fluid administration means and the other of said elements with said source of fluid, each of said elements having a central fluid manifold that is sealed at one end and in fluid comunication with said respective administration means on said source of fluid at an opposite end, said manifolds having a plurality of spacially separate access ports secured thereto and extending outwardly therefrom, each said access port being in fluid communication with said manifold and having a removable cover means at an outer free end of same, which cover means maintains said access ports sterile while in place; said access ports of one element being associable with the access ports on the other of said elements;

(d) removing the cover means from the access ports of each connector nearest the sealed end of same and bringing said two end access ports into fluid communicating association, whereby fluid communication is established between said fluid supply and said patient;

(e) at a desired time, interrupting fluid flow to the patient by severing the manifold on each element between the associated access ports and a further access port and sealing the manifold adjacent thereto, whereby the associated access ports are removed from the elements;

(f) when reinstitution of fluid flow is desired, removing the cover means from an access port on each element and bringing said two access ports into fluid communication association, whereby fluid flow to the patient is reinstituted without the possibility of reuse of a contaminated connector.

10. The method as defined in claim 9 wherein the manifolds are thermally sealed adjacent the point of severance of the associated access ports.

11. The method as defined in claim 10 wherein severance of the manifolds and sealing of same is achieved in a single operation.

12. The method as defined in claim 9 wherein severance and thermal sealing of the manifolds is located along the manifolds between the associated access ports and the next adjacent access ports on the manifolds.

* * * * *

UNITED STATES PATENT AND TRADEMARK OFFICE
CERTIFICATE OF CORRECTION

PATENT NO. : 4,298,001
DATED : November 3, 1981
INVENTOR(S) : Thomas S. Hargest, III. and William C. Ryan, Jr.

It is certified that error appears in the above-identified patent and that said Letters Patent are hereby corrected as shown below:

Column 6, line 11, "as" should read--at--.

Column 6, line 26, "connected" should read--connect--.

Column 6, line 41, "parts" should read--ports--.

Column 7, Claim 1, line 16, "acess" should read--access--.

Column 7, Claim 4, line 37, "parts" should read--ports--.

Signed and Sealed this

Nineteenth Day of January 1982

[SEAL]

Attest:

*Attesting Officer*

GERALD J. MOSSINGHOFF

*Commissioner of Patents and Trademarks*